United States Patent
Masaki (10) Patent No.: US 7,258,443 B2
(45) Date of Patent: Aug. 21, 2007

(54) OPHTHALOMOLOGIC APPARATUS (75) Inventor: Toshifumi Masaki, Tochigi-ken (JP)

(73) Assignee: Canon Kabushiki Kaisha, Tokyo (JP)

( * ) Notice: Subject to any disclaimer, the term of this patent is extended or adjusted under 35 U.S.C. 154(b) by 299 days.

(21) Appl. No.: 11/151,813

(22) Filed: Jun. 13, 2005

(65) Prior Publication Data
US 2005/0275804 A1 Dec. 15, 2005

(30) Foreign Application Priority Data
Jun. 14, 2004 (JP) ............... 2004-175595

(51) Int. Cl.
A61B 3/14 (2006.01)
(52) U.S. Cl. .............. 351/208; 351/206; 351/212
(58) Field of Classification Search ......... 351/205, 351/206, 208–212, 221
See application file for complete search history.

(56) References Cited
U.S. PATENT DOCUMENTS
6,733,129 B2 * 5/2004 Masaki ............... 351/208
2002/0036749 A1 * 3/2002 Isogai ............... 351/206

FOREIGN PATENT DOCUMENTS
JP 9-66027 A 3/1997
JP 9-84760 3/1997
JP 9-131314 A 5/1997

* cited by examiner

Primary Examiner—Huy Mai
(74) Attorney, Agent, or Firm—Morgan & Finnegan LLP (57) ABSTRACT In order to accurately align an eye examining portion with the center of the pupil, (a) the interval d between illumination light source images PL and PR is an interval obtained when the operation distance has been properly position-aligned by other alignment means. (b) shows an interval d1 in a state in which the operation distance is longer than to a proper position, and (c) shows an interval d2 in a state in which the operation distance is shorter than the proper position. Even if the operation distance fluctuates when position alignment is effected with the center of the pupil, whereby the interval becomes d1 and d2 as shown in (b) and (c), a measuring portion is moved in front to rear direction and is made coincident with the reference interval d, as shown in (a), whereby a proper operation distance is obtained.

5 Claims, 7 Drawing Sheets

OPHTHALOMOLOGIC APPARATUS

BACKGROUND OF THE INVENTION

1. Field of the Invention

This invention relates to a suitable technique for an ophthalmologic apparatus which automatically effects the position alignment of an eye to be examined and the pupil center of an eye examining portion to thereby effect eye examination and photographing.

2. Related Background Art

As a conventional ophthalmologic apparatus for effecting auto alignment, there is known one which projects a light beam from within the measurement optical axis of an eye examining portion to the cornea of an eye to be examined, detects the reflected light thereof by a light receiving element, detects the positional displacement between the eye to be examined and the eye examining portion on the basis of the detected reflected image, and drives the eye examining portion to thereby effect auto alignment.

Also, as disclosed in Japanese Patent Application Laid-open No. H09-066027, there is known an apparatus which detects the pupil center and effects auto alignment in vertical and left to right directions, and as disclosed in Japanese Patent Application Laid-open No. H09-131314, there is known an apparatus which effects alignment detection in a front to rear direction by the interval of the cornea reflected image of an anterior ocular illumination light source.

In the aforedescribed conventional examples, when they are applied, for example, to an objective type eye refractive power measuring apparatus in which it is required to effect measurement at the center of the pupil, alignment detection in vertical and left to right directions is effected at the center of the pupil and alignment detection in a front to rear direction is effected by separating the cornea reflected light beam of alignment light, as disclosed in Japanese Patent Application Laid-open No. H09-84760.

If in this case, an alignment light source and a measurement light source are used in common, the range within which the reflected light of alignment light from the cornea of an eye to be examined can be detected by a light receiving element will become narrow because the light beam of the measurement light source is thin.

Regarding the alignment detection in the front to rear direction, as disclosed in Japanese Patent Application Laid-open No. H09-131314, there is a detecting method using the interval of the cornea reflected image of anterior ocular illumination, but in this method, the interval of the corneal reflected image of the anterior ocular illumination is varied by the radius of curvature of the cornea.

SUMMARY OF THE INVENTION

The present invention has as its object to provide a suitable technique for an ophthalmologic apparatus which automatically effects the position alignment of an eye to be examined and the pupil center of an eye examining portion to thereby effect eye examination and photographing.

In order to solve the above-noted problems, an ophthalmologic apparatus according to the present invention is characterized by alignment light beam projection means for projecting an alignment light beam onto the cornea of an eye to be examined, alignment light beam detection means for detecting the cornea reflected light of the alignment light beam, a plurality of illumination means for illuminating the anterior ocular of the eye to be examined, image sensing means for sensing on image-picking up the anterior ocular of the eye to be examined, pupil position detection means for detecting the pupil position of the eye to be examined from the image of the anterior ocular picked up by the image sensing means, cornea reflected image interval detection means for detecting the interval between the plurality of cornea reflected images of the illumination means, first position alignment means for detecting the position of the eye to be examined by the cornea reflected light detected by the alignment light beam detection means to thereby effect the position alignment of an eye examining portion and the eye to be examined, memory means for storing therein as a reference interval the interval between the plurality of cornea reflected images detected by the cornea reflected image interval detection means when the position alignment by the first position alignment means has been completed, second position alignment means for aligning the eye examining portion with the pupil position detected by the pupil position detection means, and third position alignment means for detecting the positional displacement of the eye to be examined in a front to rear direction on the basis of the relation between the interval detected by the cornea reflected image interval detection means and the reference interval stored in the memory means to thereby effect the position alignment of the eye examining portion and the eye to be examined in the front to rear direction.

Other features and advantages of the present invention will become apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate an embodiment of the invention and, together with the description, serve to explain the principles of the invention.

DESCRIPTION OF THE PREFERRED EMBODIMENT

A preferred embodiment of the present invention will now be described in detail with reference to the accompanying drawings.

The present invention will hereinafter will be described in detail with respect to the shown embodiment thereof.

Figure 1:
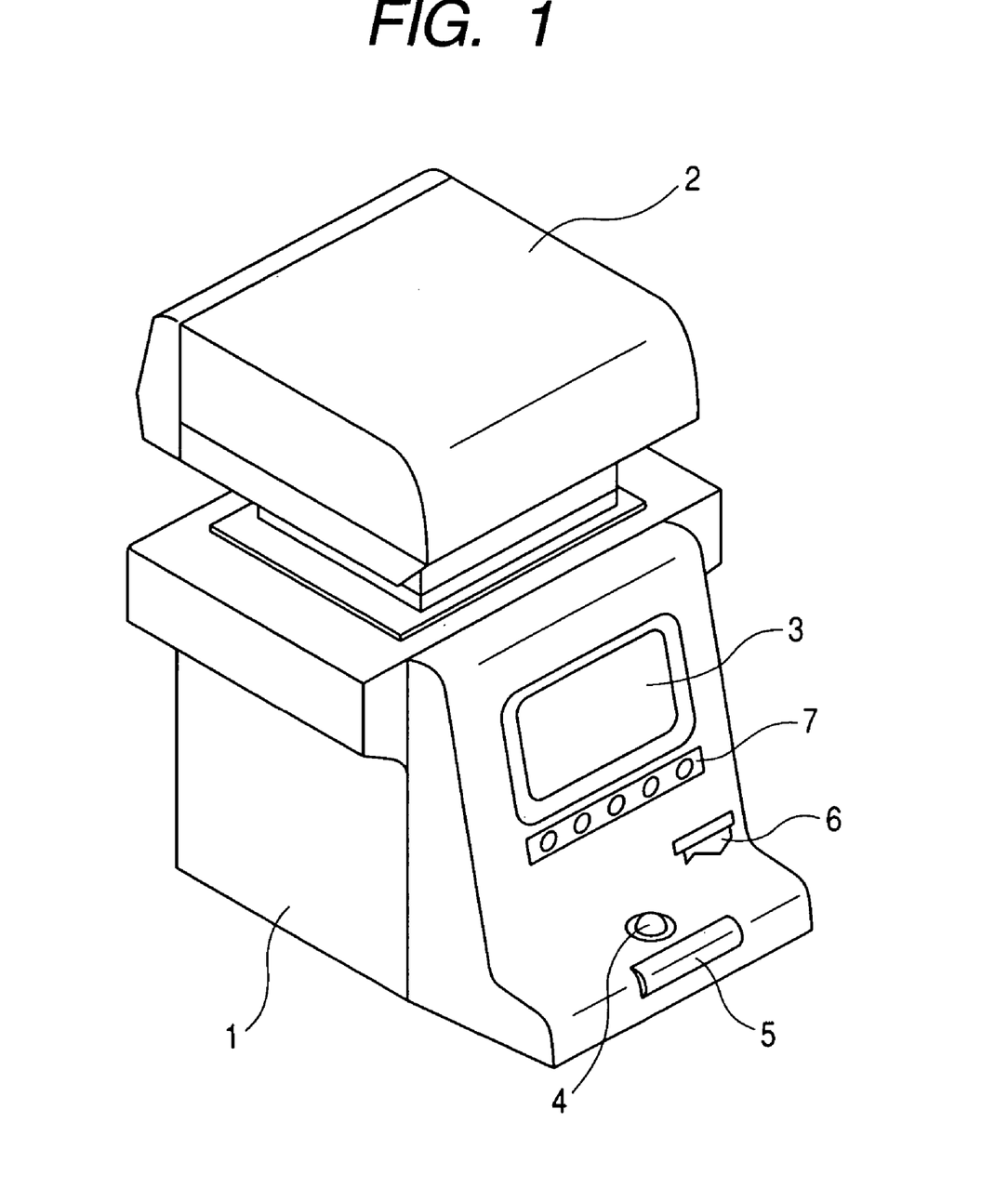
FIG. 1 is a pictorial view of the embodiment.

FIG. 1 is a pictorial view of the eye refraction measuring apparatus of the present invention. A measuring portion 2 is movably placed on a base stand 1, and on the operating surface of the base stand 1, there are provided a monitor comprising a liquid crystal or a CRT for selecting the display of a measurement value, the image of an eye to be examined, etc. and the setting of various devices, a track ball 4 for operating the display screen and for position-aligning the measuring portion 2 with the eye to be examined, a roller 5, a printer 6 for printing the result of measurement, and a switch panel 7 having a measurement starting switch, a selection setting switch, etc. disposed thereon.

The measuring portion is adapted to be movable in vertical, left to right and front to rear directions relative to the base stand 1 by a three-shaft motor contained therein.

Figure 2:
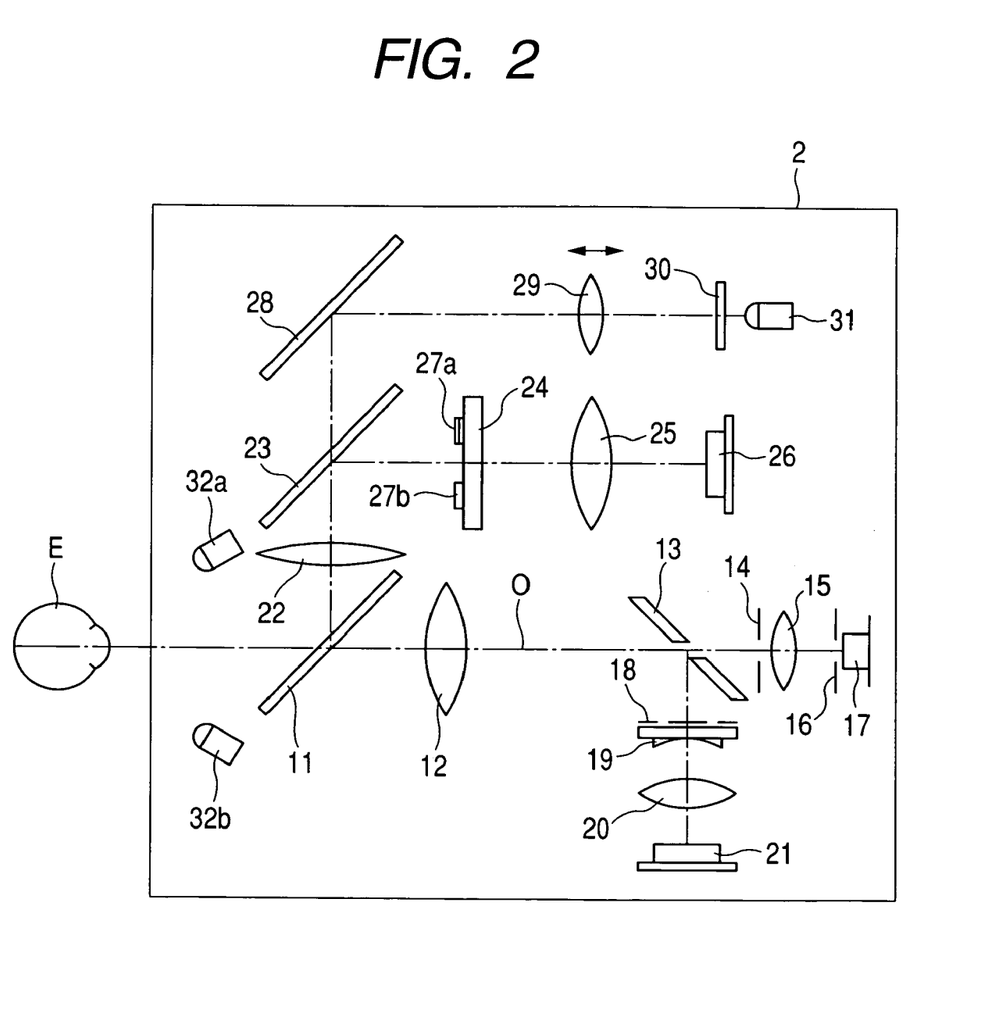
FIG. 2 shows the optical construction of a measuring portion.
Figure 3:
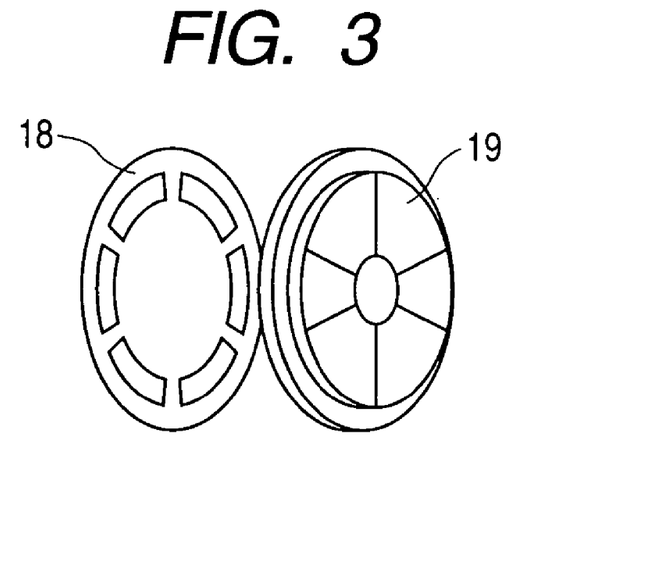
FIG. 3 is a perspective view of a six-division stop and a six-division prism.

FIG. 2 shows the internal construction of the measuring portion. On the center axis O of the measuring portion 2 position-aligning with the visual axis of the eye E to be examined, there are disposed as an eye refraction measuring optical system a dichroic mirror 11 for totally reflecting visible light and partly reflecting a light beam of a wavelength 880 nm, an objective lens 12, an apertured mirror 13, a stop 14, a projection lens 15, a projection stop 16 and a measurement light source 17 emitting a light beam of wavelength 880 nm. In the reflecting direction of the apertured mirror 13, there are arranged a six-division stop 18, a six-division prism 19, a light receiving lens 20 and a two-dimensional image sensing element 21. FIG. 3 shows a perspective view of the six-division stop 18 and the six-division prism 19, and actually the six-division stop 18 and the six-division prism 19 are brought into close contact with each other.

On the other hand, in the reflecting direction of the dichroic mirror 11, there are disposed a light receiving optical system and a fixation target projection optical system in which anterior ocular observation and alignment detection are used in common. A lens 22 and a dichroic mirror 23 are disposed in the light receiving optical system, and in the reflecting direction of the dichroic mirror 23, there are arranged as an alignment optical system an alignment prism stop 24, an imaging lens 25 and a two-dimensional image sensing element 26.

Figure 4:
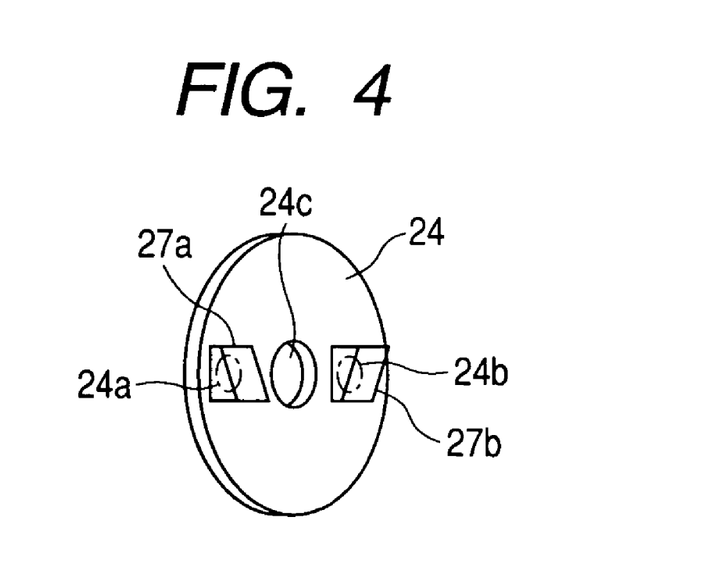
FIG. 4 is a perspective view of an alignment prism stop.

FIG. 4 shows a perspective view of the alignment prism stop 24, and three opening portions 24*a*, 24*b* and 24*c* are provided in a straight line on a disk-shaped stop plate, and alignment prisms 27*a* and 27*b* for deflecting a light beam are adhesively secured to those sides of the opening portions 24*a* and 24*b* on the opposite sides which are adjacent to the dichroic mirror 23.

Further, on the transmitting side of the dichroic mirror 23, there are arranged a total reflection mirror 28, a fixation guide lens 29, a fixation chart 30 and a fixation target light source 31, whereby a fixation projection optical system is constituted. Also, obliquely forwardly of the eye E to be examined, illumination light sources 32*a* and 32*b* are provided symmetrically with respect to the optical path O.

Figure 5:
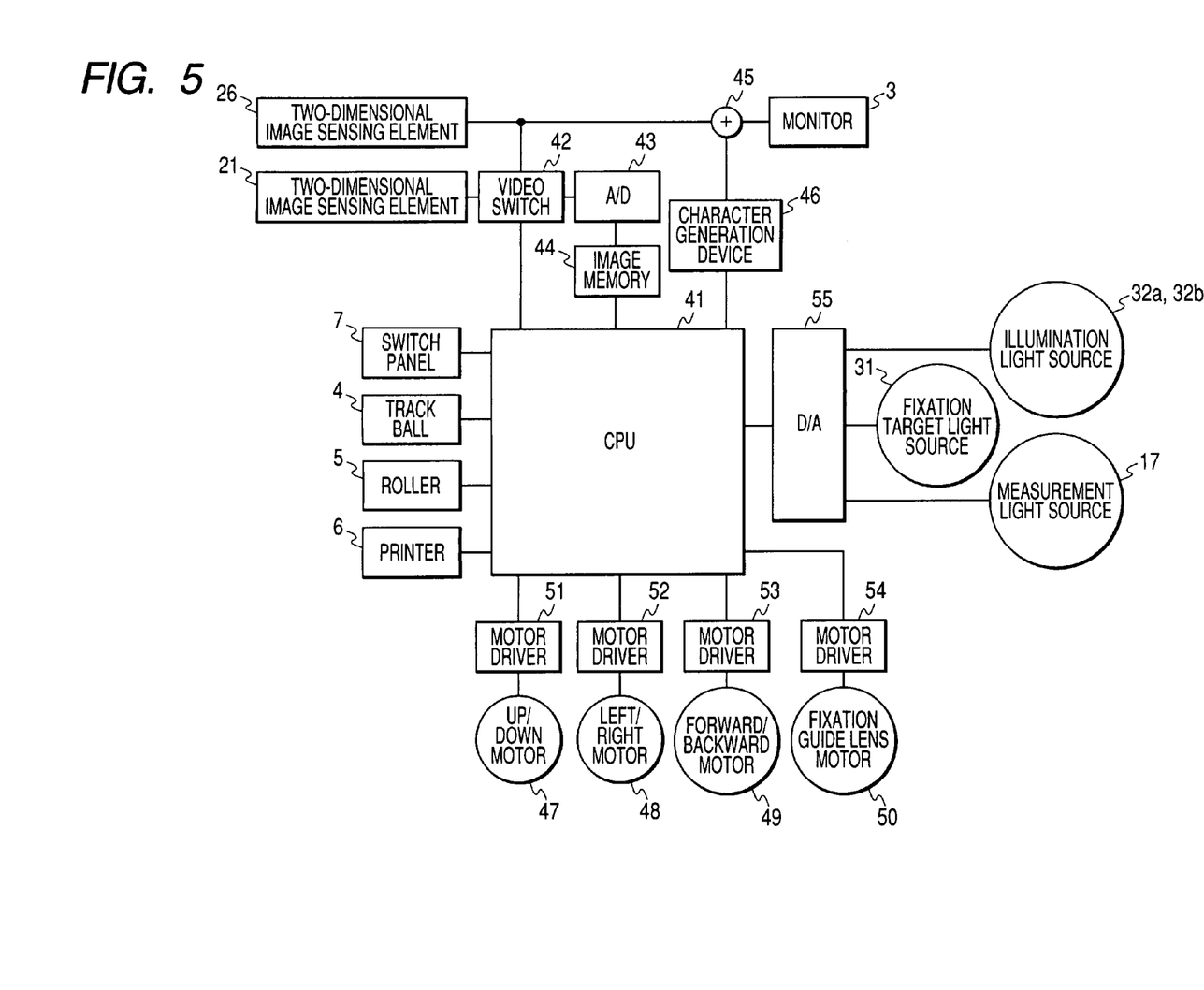
FIG. 5 is a block circuit construction diagram of a control system.

FIG. 5 is a block circuit construction diagram of a control system. The switch panel 7, the track ball 4, the roller 5 and the printer 6 are connected to the ports of a CPU 41.

The outputs of the two-dimensional image sensing elements 21 and 26 are inputted to a video switch 42, which in turn is adapted to select the signal of one of the two-dimensional image sensing elements 21 and 26 by the command of the CPU 41, and output it to an A/D converter 43. Digital data from the A/D converter 43 is connected to an image memory 44, which in turn is connected to the CPU 41. Also, the output of the two-dimensional image sensing element 26 is connected to an adder 45, in which it is added to the output of a character generator 46 through the CPU 41, and is connected to the monitor 3.

An up-and-down motor 47, a left-to-right motor 48, a front-to-rear motor 49 and a fixation guide lens motor 50 for moving the measuring portion 2 are connected to motor drivers 51, 52, 53 and 54, respectively, and are driven by a command from the CPU 41. The measurement light source 17, the fixation target light source 31 and the illumination light sources 32*a* and 32*b* are connected to a D/A converter 55 through drivers, not shown, and are adapted to be capable of changing the quantity of light by a command from the CPU 41.

The projection light beam of the fixation target light source 31 illuminates a fixation chart 30 from the back side thereof during fixation guide, and is projected onto the eye E to be examined through the fixation guide lens 29 and the lens 22. The fixation guide lens 29 are adapted to be movable in the direction of the optical axis thereof by the rotation of the fixation guide lens motor 50 so as to be capable of coping with any change in the visibility of the eye E to be examined.

In the thus constructed eye refraction measuring apparatus, in case of the measuring operation, an operator operates the track ball 4 and the roller 5 in order to place an examiner's face on a face receiving stand provided forwardly of the measuring portion 2, and adjust the optical axis O of the measuring portion 2 to the eye to be examined E. The track ball 4 moves the measuring portion 2 to the left to right and front to rear directions relative to the eye to be examined E, and the roller 5 moves the measuring portion 2 in the vertical direction to thereby effect position alignment.

In this operation, output signals from a pulse counter and a rotary encoder contained in the track ball 4 and the roller 5, respectively, are received by the CPU 41 to thereby detect an operation amount and a speed. Further, from the operation amount and speed, the up-and-down motor 47, the left-to-right motor 48 and the front-to-rear motor 49 are driven through the respective motor drivers 51, 52 and 53.

The light source of the wavelength 880 nm for alignment detection is used in common with the measurement light source 17, and an alignment light beam from the measurement light source 17 is reflected by the cornea of the eye E to be examined. This reflected light beam is reflected by the dichroic mirror 11, passes through the lens 22, is reflected by the dichroic mirror 23 and is directed to the alignment optical system.

Figure 6A:
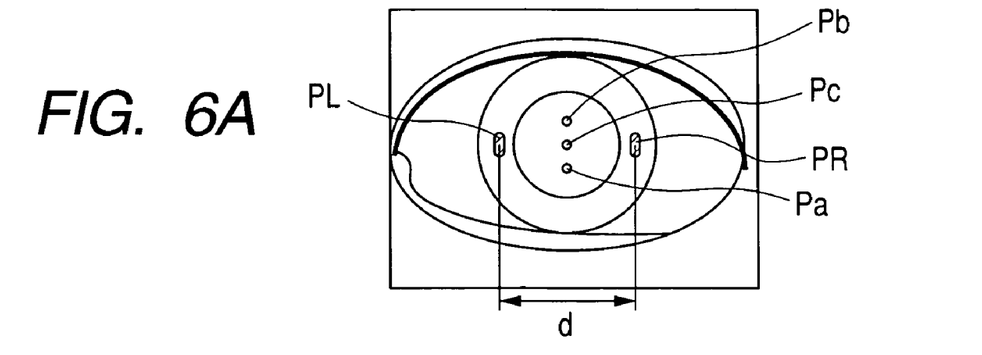
FIGS. 6A, 6B and 6C are illustrations of a luminescent point by the cornea reflected image of alignment light and a cornea reflected image by an illumination light source appearing in an anterior ocular image.
Figure 6B:
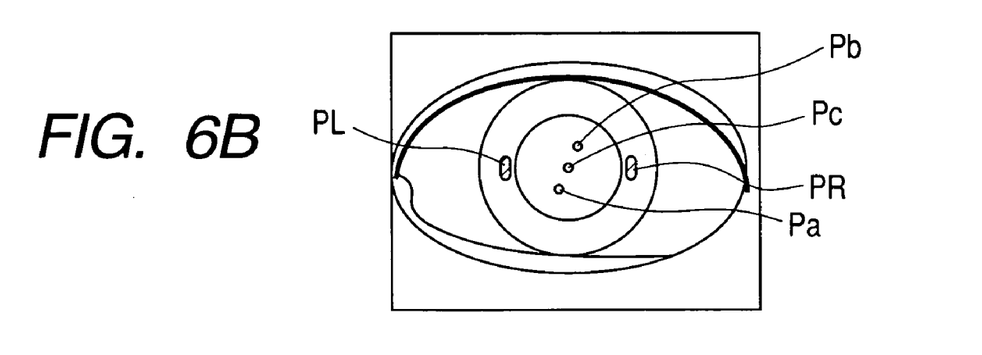
Figure 6C:
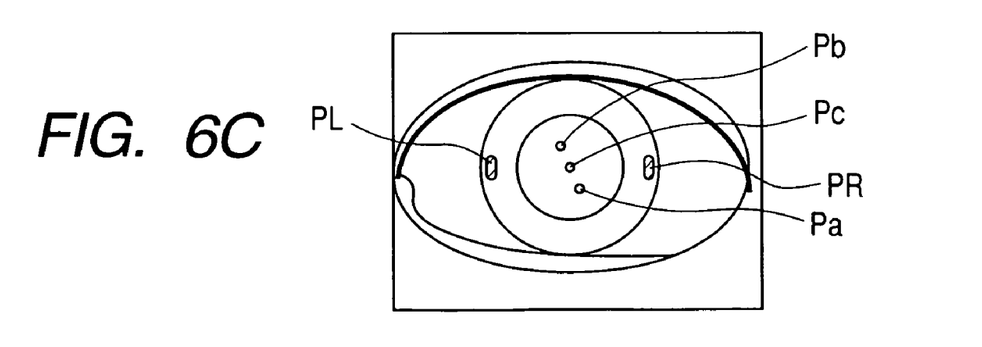

FIGS. 6A to 6C show the anterior ocular image of the eye E to be examined observed when the cornea reflected image of the measurement light source 17 is used for alignment detection, and the three luminescent points Pa to Pc of the cornea reflected image are arranged in a substantially vertical direction at the central portion of the cornea. A light beam transmitted through the opening portion 24*a* of the alignment prism stop 24 becomes the lower luminescent point Pa, a light beam transmitted through the opening portion 24*b* becomes the upper luminescent point Pb, and a light beam transmitted through the central opening portion 24*c* becomes a central luminescent point Pc.

FIG. 6A shows a case where the luminescent points Pa to Pc are vertically arranged in a line, and the operation distance of the eye E to be examined is properly position-aligned, FIG. 6B shows an observed image in a state in which the operation distance between the eye E to be examined and the measuring portion 2 is longer than to a proper position, and FIG. 6C shows the observed image in a state in which the operation distance between the eye E to be examined and the measuring portion 2 is shorter than the proper position. The alignment displacement amount of alignment in the operation distance direction thereof is calculated from the displacement of the X coordinates of the upper and lower luminescent points Pa and Pb of the three luminescent points Pa to Pc, and the alignment displacement amounts in the vertical and left to right directions are calculated from the position of the central luminescent point Pc.

When it is confirmed by the monitor 3 that the luminescent points Pa to Pc have been obtained, and the measurement starting switch is depressed, the CPU 41 starts auto alignment in which the measuring portion 2 is automatically position-aligned into a state as shown in FIG. 6A relative to the eye E to be examined.

Figure 7:
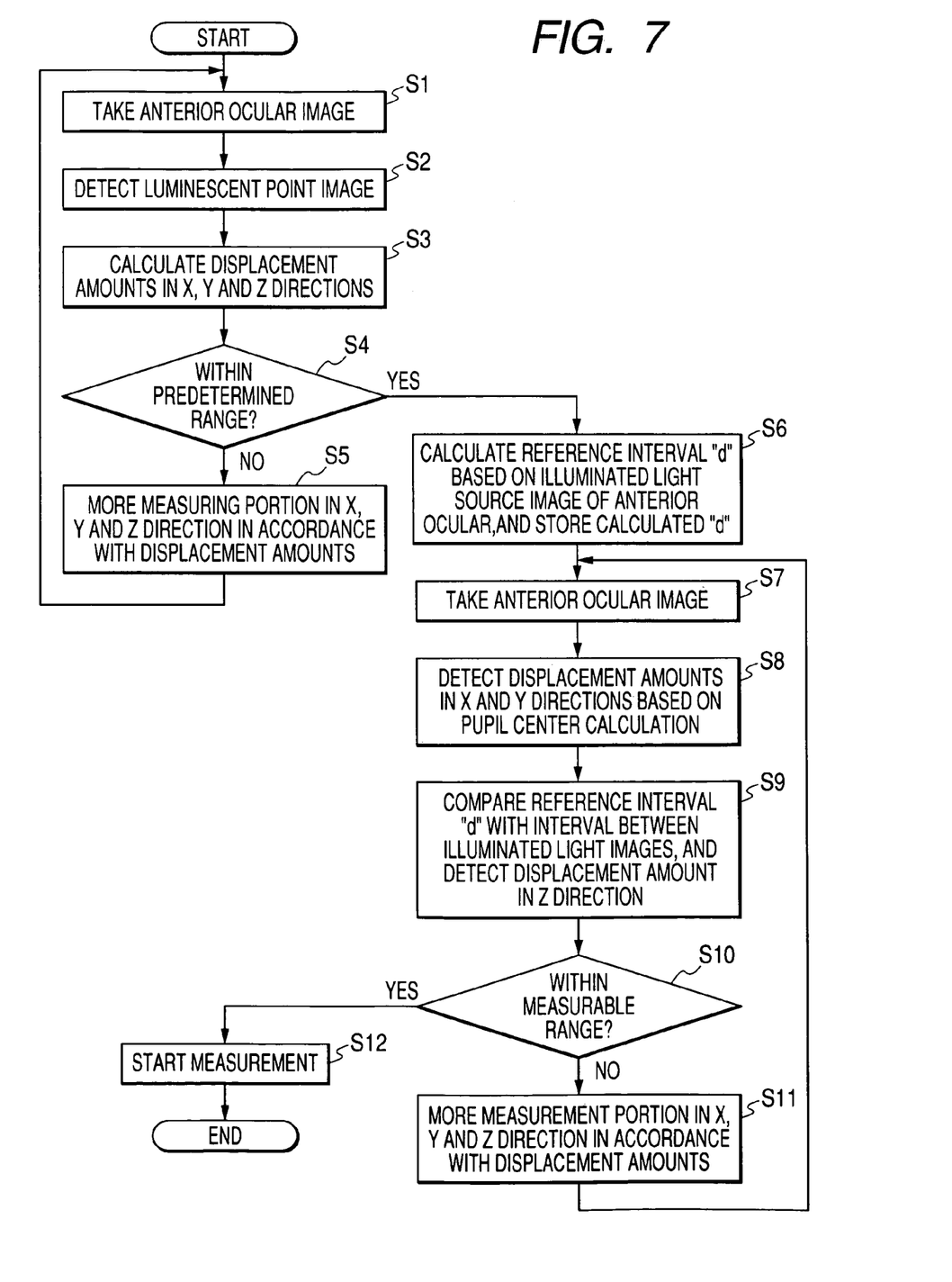
FIG. 7 is an operation flow chart from the start till the completion of alignment.

FIG. 7 is a flow chart of a series of operations from the start till the completion of the auto alignment. X direction means the left to right direction, Y direction means the vertical direction, and Z direction means the operation distance. In the position alignment of the eye E to be examined and the measuring portion 2 by the cornea reflected light of the above-described alignment light, at a step S1, an image sensed or picked up by the two-dimensional image sensing element 26 is introduced into the image memory 44. At a step S2, the detection of the luminescent points Pa to Pc by the measurement light source 17 is effected from the image of the anterior ocular introduced into the image memory 44, by the CPU 41. At a step S3, position displacement amounts in X, Y and Z directions are calculated from the positions of the luminescent points Pa to Pc by the CPU 41.

At a step S4, judgment as to whether the calculated position displacement amounts in X, Y and Z directions are within a predetermined allowable range is effected, and if they are outside the predetermined allowable range, shift is made to a step S5. This predetermined allowable range in Z direction is such a degree of range as does not affect the measurement, and in X and Y directions, measurement is not effected at the position of the vertex of the cornea and therefore, the allowable range in these directions may be made wider than the allowable range in Z direction. At the step S5, the up-and-down, left-to-right and front-to-rear motors 47, 48 and 49 are driven in conformity with the position displacement amounts in X, Y and Z directions by the command of the CPU 41 to thereby move the measuring portion 2, and return is made to the step S1, where the auto alignment operation is continued.

The loop of the step S1 to the step S5 is repeated until it is judged at the step S4 that the position displacement amounts in X, Y and Z directions are within the predetermined allowable range, that is, until the luminescent points Pa to Pc are vertically arranged in a line as shown in FIG. 6A, and the position displacement amounts come within the predetermined range, shift is made to a step S6.

On the other hand, together with the anterior ocular image of the eye E to be examined by the illumination light sources 32a and 32b, by the cornea reflected image by the light beam transmitted through the central opening portion 24c of the alignment prism stop 24 by the illumination light sources 32a and 32b, illumination light source images PL and PR are formed on the left and right of the pupil, as shown in FIGS. 6A to 6C.

At the step S6, in a state in which the image in the image memory 44, i.e., the alignment displacement in Z direction, when it has been judged at the step S4 by the use of luminescent points Pa to Pc that the aforementioned position displacement amounts are within the predetermined allowable range, is within a measurable allowable range, and there is little or no alignment displacement in Z direction in which as shown in FIG. 6A, the three luminescent points Pa to Pc of the cornea reflected image by the measurement light source 17 are properly arranged in the vertical direction, the interval between the two illumination light source images PL and PR of the illumination light sources 32a and 32b on the opposite sides is found, and is stored as a reference interval d, whereafter shift is made to a step S7.

At the step S7, as at the step S1, the image picked up by the two-dimensional image sensing element 26 is introduced into the image memory 44. At a step S8, the pupil which becomes a black image is discriminated from the anterior ocular image introduced into the image memory 44 at the step S1, and from the centroid of this pupil, the center thereof is detected by the CPU 41, and position displacement amounts in X and Y directions are detected from the center coordinates of this pupil, and then the measuring portion 2 is moved to the center of the pupil. The detection of the center of this pupil is done because the aforedescribed detection by the luminescent points Pa to Pc is the detection of the vertex of the cornea and in some cases, the pupil is eccentric from the vertex of the cornea.

This movement of the measuring portion 2 to the center of the pupil is effected by the measuring portion 2 being moved in X and Y directions by the up-and-down and left-to-right motors 47 and 48, respectively, but sometimes, the distance in Z direction may also be varied by the movement or the like of the eye E to be examined during this adjustment. Also, some of the luminescent points Pa to Pc at this time cannot be detected, and so, at a step S9, the interval between the illumination light source images PL and PR is calculated from the anterior ocular image introduced into the image memory 44 by the CPU 41, and the detection of the alignment displacement in Z direction is effected again.

Figure 8A:
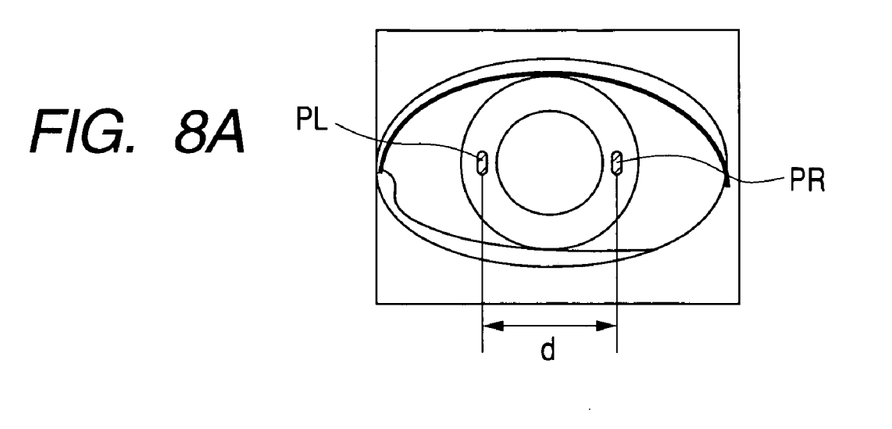
FIGS. 8A, 8B and 8C are illustrations of the cornea reflected image of the illumination light source.
Figure 8B:
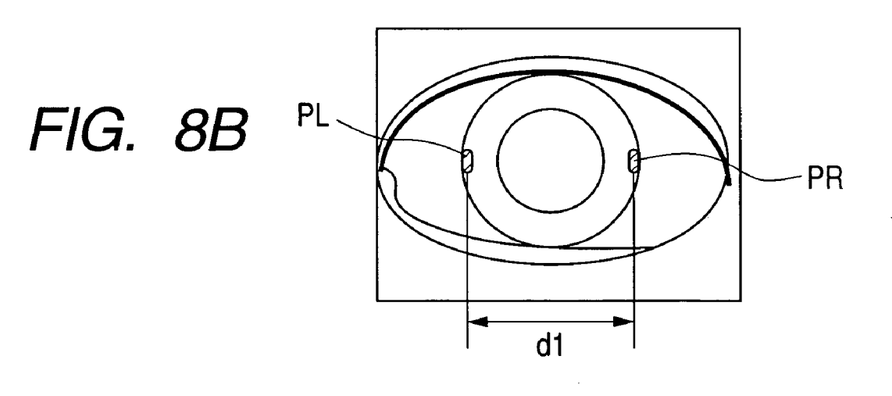
Figure 8C:
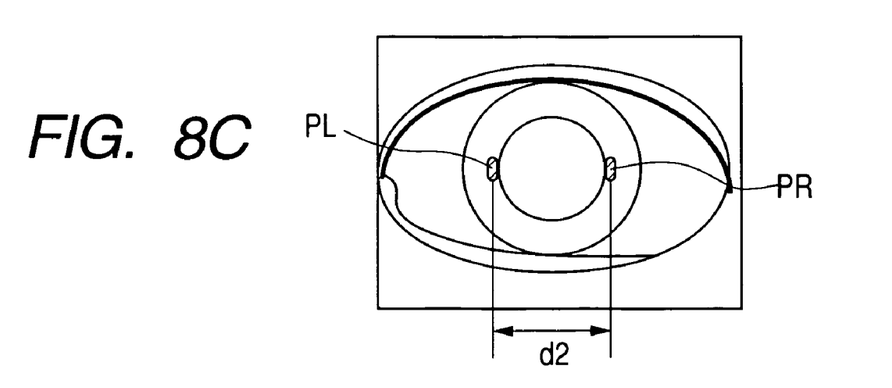

FIG. 8A shows the anterior ocular in a case where the interval between the illumination light source images PL and PR is d and the operation distance of the measuring portion 2 is properly position-aligned. FIG. 8B shows the anterior ocular image of the eye E to be examined in a state in which the operation distance between the eye E to be examined and the measuring portion 2 is longer than to the proper position, and the interval between the illumination light source images PL and PR becomes d1, and at this time, the longer becomes the operation distance, the narrower becomes the interval d1. FIG. 8C shows the anterior ocular image of the eye E to be examined in a state in which the operation distance between the eye E to be examined and the measuring portion 2 is shorter than to the proper position, and the interval between the illumination light source images PL and PR becomes d2, and the shorter becomes the operation distance, the wider becomes the interval d2.

The degree of this interval is also changed by the radius of curvature of the cornea, but if the measuring portion 2 is moved in Z direction, i.e., in the front to rear direction, by the front-to-rear motor 49 so that the interval may become d which has previously been defined as the proper operation distance, and the interval d is made coincident with the stored reference interval d as shown in FIG. 8A, a proper operation distance will be obtained.

At a step S10, whether the position displacement amounts in X, Y and Z directions calculated at the steps S8 and S9 are within a measurable range is judged, and if they are outside the measurable range, shift is made to a step S11. At the step S11, the up-and-down, left-to-right and front-to-rear motors 47, 48 and 49 are driven in conformity with the position displacement amounts in X, Y and Z directions by the command of the CPU 41 to thereby move the measuring portion 2, and return is made to the step S7, where the auto alignment operation is continued.

The loop of the step S7 to the step S11 is repeated until at the step S10, it is judged that the position displacement amounts in X, Y and Z directions are within the measurable range, and if they come within the measurable range, the auto alignment operation is completed, and shift is made to a step S12, where the measurement of the eye refractive power is started.

In the measurement of the eye refractive power, the light beam emitted from the measurement light source 17 in the eye refraction measuring optical system is stopped down by the projection stop 16, is primary-imaged on this side of the objective lens 12 by the projection lens 15, is transmitted through the objective lens 12 and the dichroic mirror 11 and is projected to the pupil center of the eye E to be examined. The light beam is imaged on the fundus of the eye E to be examined, and the reflected light thereof passes through the periphery of the pupil and returns to the objective lens 12.

The light beam reflected by the apertured mirror 13 is divided into six by the six-division stop 18, and is refracted by the six-division prism 19 so as to be received by the proper range of the light receiving surface area of the two-dimensional image sensing element 21, and projects six spot images onto the two-dimensional image sensing element 21. An eye refraction value is then calculated by known means on the basis of the positions of the spot images obtained by the two-dimensional image sensing element 21.

While in the present embodiment, the measurement of the eye refractive power is effected after the auto alignment operation has been completed, the measurement of the eye refractive power takes some degree of time for a clouding operation or the like and during the measurement, alignment displacement may occur and therefore, the measurement may be carried out while auto alignment is continued.

According to the present invention, there can be provided a suitable technique for an ophthalmologic apparatus which automatically effects the position alignment of an eye to be examined and the pupil center of an eye examining portion to thereby effect eye examination and photographing.

As many apparently widely different embodiments of the present invention can be made without departing from the spirit and scope thereof, it is to be understood that the invention is not limited to the specific embodiment thereof except as defined in the claims.

This application claims priority from Japanese Patent Application No. 2004-175595 filed Jun. 14, 2004, which is hereby incorporated by reference herein.

What is claimed is:

1. An ophthalmologic apparatus comprising:
   alignment light beam projection means for projecting an alignment light beam onto a cornea of an eye to be examined:
   alignment light beam detection means for detecting the cornea reflected light of said alignment light beam;
   a plurality of illumination means for illuminating the anterior ocular of the eye to be examined;
   image sensing means for sensing the anterior ocular of the eye to be examined;
   pupil position detection means for detecting the pupil position of the eye to be examined from the image of the anterior ocular sensed by said image sensing means, cornea reflected image interval detection means for detecting an interval between the plurality of cornea reflected images of said illumination means;
   first position alignment means for detecting the position of the eye to be examined by the cornea reflected light detected by said alignment light beam detection means to thereby effect the position alignment of an eye examining portion and the eye to be examined;
   memory means for storing therein as a reference interval said interval between said plurality of cornea reflected images detected by said cornea reflected image interval detection means when the position alignment by said first position alignment means has been completed;
   second position alignment means for aligning said eye examining portion with said pupil position detected by said pupil position detection means; and
   third position alignment means for detecting the positional displacement of the eye to be examined in a front to rear direction on the basis of a relation between said interval detected by said cornea reflected image interval detection means and said reference interval stored in said memory means to thereby effect the position alignment of said eye examining portion and the eye to be examined in the front to rear direction.

2. An ophthalmologic apparatus according to claim 1, wherein said alignment light beam detection means is used in common with said image sensing means.

3. An ophthalmologic apparatus according to claim 1, wherein said alignment light beam projection means is used in common with a measurement light source for eye examination.

4. An ophthalmologic apparatus according to claim 1, wherein said first position alignment means adjusts the position of said eye examining portion so that the three luminescent points of said cornea reflected light may be vertically arranged in a line.

5. An ophthalmoloaic apparatus according to claim 1, wherein said second position alignment means adjusts the position of said eye examining portion so as to coincide with a center position by the centroid of the pupil obtained by said pupil position detecting means.

* * * * *